United States Patent [19]
Lord et al.

[11] Patent Number: 5,569,186
[45] Date of Patent: Oct. 29, 1996

[54] CLOSED LOOP INFUSION PUMP SYSTEM WITH REMOVABLE GLUCOSE SENSOR

[75] Inventors: Peter C. Lord, Santa Clarita; Fredric C. Coleman, Granada Hills, both of Calif.

[73] Assignee: Minimed Inc., Sylmar, Calif.

[21] Appl. No.: 231,800

[22] Filed: Apr. 25, 1994

[51] Int. Cl.$^6$ .................................................. A61M 31/00
[52] U.S. Cl. ............................... 604/67; 604/66; 128/637; 128/635
[58] Field of Search .................... 604/65–67, 50; 128/DIG. 13, 632, 635, 637

[56] References Cited

U.S. PATENT DOCUMENTS

| | | | |
|---|---|---|---|
| 3,837,339 | 9/1974 | Aisenberg et al. . | |
| 4,055,175 | 6/1977 | Clemens | 604/66 |
| 4,538,616 | 9/1985 | Rogoff | 128/632 |
| 4,543,955 | 10/1985 | Schroeppel | 128/635 |
| 4,573,994 | 3/1986 | Fischell et al. . | |
| 4,633,878 | 1/1987 | Bombardieri . | |
| 4,650,547 | 2/1987 | Gough . | |
| 4,671,288 | 6/1987 | Gough . | |
| 4,703,756 | 11/1987 | Gough et al. . | |
| 4,781,798 | 11/1988 | Gough . | |
| 4,822,337 | 4/1989 | Newhouse | 604/66 |
| 4,890,620 | 1/1990 | Gough . | |
| 4,979,015 | 12/1990 | Hakky | 604/66 |
| 4,985,015 | 1/1991 | Obermann | 604/67 |
| 5,101,814 | 4/1992 | Palti . | |
| 5,174,291 | 12/1992 | Schoonen | 128/637 |
| 5,269,301 | 12/1993 | Cohen | 604/66 |
| 5,328,460 | 7/1994 | Lord | 604/67 |
| 5,337,747 | 8/1994 | Neftel | 128/637 |
| 5,368,028 | 11/1994 | Palti | 604/66 |
| 5,372,133 | 12/1994 | Hogen Esch . | |

*Primary Examiner*—Randall L. Green
*Assistant Examiner*—Chalin Smith
*Attorney, Agent, or Firm*—Kelly, Bauersfeld & Lowry

[57] ABSTRACT

An infusion pump system includes a removable in vivo glucose sensor for monitoring glucose concentration level in a patient, and for signaling an infusion pump to deliver a selected medication such as insulin to a patient. The glucose sensor comprises a sensor cable for placement through a catheter to position a distal sensor tip at a selected in vivo sensor site. A proximal end of the sensor cable seats within a connector fitting mounted on the catheter at a convenient and accessible subcutaneous position. The connector fitting couples the sensor cable to an implanted control unit which signals the infusion pump to deliver the patient medication. In a preferred system, the infusion pump is also implanted and receives control signals via a direct or telemetric connection. The sensor cable is easily accessed at the connector fitting for periodic sensor removal and replacement, without requiring removal or replacement of other system components.

9 Claims, 2 Drawing Sheets

CLOSED LOOP INFUSION PUMP SYSTEM
WITH REMOVABLE GLUCOSE SENSOR

BACKGROUND OF THE INVENTION

This invention relates generally to infusion pump systems for programmed operation to deliver a selected medication to a patient, particularly of the type including an infusion pump implanted directly into the body of the patient. More specifically, this invention relates to an improved system having an implanted glucose sensor adapted for convenient sensor removal and replacement on a periodic basis.

Medication infusion pumps are generally known in the art for use in delivering a selected medication to a patient in a scheduled or preprogrammed manner. In recent years, such infusion pumps have been developed in compact form adapted for direct implantation into the body of a patient, and to deliver a specific medication such as insulin to the patient in discrete doses over an extended time period. An implanted infusion pump of this general type includes an internal medication chamber for receiving and storing a supply of the selected medication in liquid form, in combination with miniature pump means and associated programmable control means for delivering the medication to the patient in accurate and repeatable doses. For one illustrative example of an implanted medication infusion pump of this general type, see U.S. Pat. No. 4,573,994.

While implantable infusion pumps have constituted a major step forward in reliable and convenient administration of certain medications, particularly insulin for a diabetic patient, practical programmed pump operation has been limited to an open loop approach involving medication dispensing in response to anticipated patient requirements. In this regard, implanted pumps have been adapted to deliver incremental doses at predetermined times and amounts in accordance with the condition and lifestyle of a particular patient. External controller devices have been developed for altering the pump program and/or for delivering a medication dose on demand, typically via a radio telemetry connection with the implanted pump. By contrast, a closed loop system involving controlled pump operation in response to actual rather than anticipated patient medication requirements, has not been available.

In recent years, considerable research and development activity has focused upon improvements in glucose sensors for monitoring glucose concentration level in a patient fluid, such as blood. These research efforts have resulted in proposals for implanted or in vivo glucose sensors designed to provide an instantaneous reading of patient glucose concentration. For examples of proposed in vivo glucose sensors, see U.S. Pat. Nos. 4,650,547; 4,671,288; 4,781,798; 4,703,756; and 4,890,620.

The availability of implantable glucose sensors enhances the feasibility of a closed loop infusion pump system wherein operation of a medication infusion pump is responsive to actual glucose concentration measurements obtained on a continuous or frequent basis. However, the service life of an implantable glucose sensor is typically relatively short in duration, on the order of a few months, whereas current infusion pump technology provides implantable components having an operating life on the order of ten years or more. A practical system designed to accommodate periodic removal and replacement of an in vivo glucose sensor, without requiring removal or replacement of other pump system components, has not been developed.

The present invention overcomes the problems and disadvantages encountered in the prior art by providing an improved infusion pump system adapted for closed loop control in response to operation of an implanted and easily removable glucose sensor.

SUMMARY OF THE INVENTION

In accordance with the invention, an infusion pump system includes a medication infusion pump for programmed operation to deliver a selected medication to a patient, in combination with an implantable glucose sensor for closed loop control of pump operation. In the preferred form, the infusion pump is also implanted within the body of the patient and is controlled automatically in response to glucose concentration measurements, by means of a direct or telemetric coupling with the sensor. The sensor is anchored within the patient by a subcutaneously mounted and easily accessed connector fitting having means for coupling or relaying sensor signals to the infusion pump. The glucose sensor is accessed at the connector fitting for relatively simple removal and replacement on an as-needed periodic basis, without requiring removal or replacement of other pump system components.

A preferred connector fitting has a generally cylindrical configuration adapted for convenient mounting beneath the patient's skin at a proximal end of a catheter leading to a selected in vivo sensor site. The glucose sensor comprises an elongated sensor cable for placement through the connector fitting and catheter to position a sensor tip at a distal end of the cable substantially at the sensor site. A proximal end of the sensor cable seats within the connector fitting and includes means such as contacts or the like for coupling with the connector fitting so that the connector fitting provides means for electrically coupling the sensor cable to the pump system. In one preferred form, the connector fitting couples the sensor cable to an implantable control unit having means for telemetering sensor measurements to the infusion pump. In another form, the connector fitting is coupled directly to the infusion pump having the control unit integrated therein for regulating pump operation.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
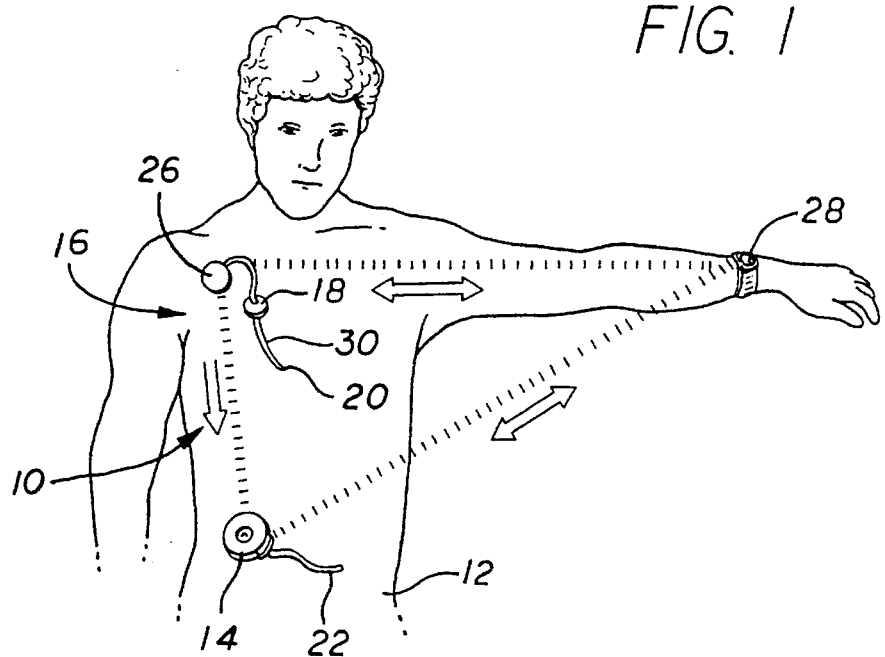
FIG. 1 illustrates, somewhat in schematic form, a closed loop infusion pump system embodying the novel features of the invention for delivering a selected medication to a patient.

As shown in the exemplary drawings, a closed loop infusion pump system referred to generally in FIG. 1 by the reference numeral 10 is provided for delivering a selected medication to a patient 12. The system 10 generally comprises an infusion pump 14 which responds to control signals from an implantable sensor unit 16 to deliver the medication as needed to the patient. In accordance with a primary aspect of the invention, the sensor unit 16 includes a subcutaneously mounted connector fitting 18 for anchoring an in vivo glucose sensor 20 in a manner permitting convenient sensor removal and replacement.

The improved infusion pump system 10 of the present invention monitors patient glucose concentration level on a continuous or frequent intermittent basis to provide appropriate control signals for closed loop control of the infusion pump 14. The selected medication such as insulin for a diabetic patient may thus be administered to the patient in response to actual patient requirements as represented by the glucose measurement. The connector fitting 18 provides a relatively simple and easily accessed structure for coupling the glucose sensor 20 with other system components, while permitting access to the glucose sensor for removal and replacement. In this regard, the glucose sensor 20 can be replaced on a periodic basis, typically at the conclusion of a service life of a few months, while permitting the remaining system components to remain undisturbed within the patient.

In a preferred system arrangement as viewed in FIG. 1, the infusion pump 10 comprises a small and substantially self-contained unit adapted for direct implantation into the body of the patient 12. The pump 14 comprises an hermetically sealed pump housing constructed typically from a biocompatiable material such as titanium to titanium alloy, and defining an internal medication chamber for receiving and storing a supply of the selected medication in liquid form, such as insulin for a diabetic patient. The pump housing further encases a miniature dispensing pump and associated electronic control circuitry in combination with a battery power supply for operating the pump to deliver medication doses to the patient via an appropriate catheter 22 or the like. The control circuitry is suitably programmed and operated to deliver the medication in accordance with individual patient need, including but not limited to closed loop response to glucose concentration measurement as will be described in more detail. In addition, the pump housing is designed to permit percutaneous refilling of the internal medication chamber without requiring surgical access to the implanted pump. For a more detailed description of the overall construction and operation of implantable infusion pumps of this general type, see U.S. Pat. Nos. 4,373,527 and 4,573,994, which are incorporated by reference herein.

Figure 2:
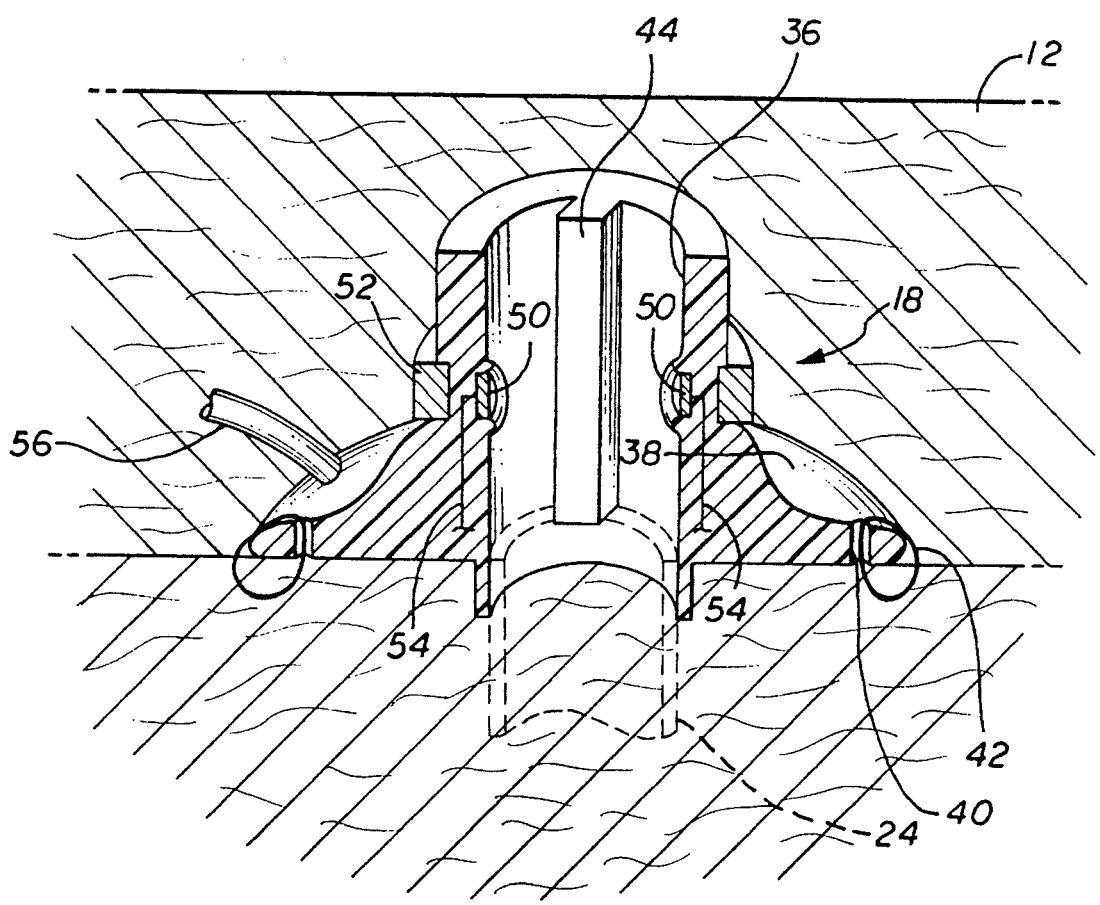
FIG. 2 is an enlarged fragmented sectional view depicting a subcutaneously mounted connector fitting for use in the infusion pump system.

The sensor unit 16 is also implanted within the patient 12 at a selected position for placement of the glucose sensor 20 in contact with a patient fluid, such as in intimate contact with patient blood within a cephalic vein. The sensor unit 16 generally comprises the connector fitting 18 mounted at proximal end of an elongated catheter 24 (FIG. 2). The connector fitting 18 is located at a convenient subcutaneous site for relatively easy palpable identification, whereas the catheter 24 extends from the connector fitting to a distal end positioned at a selected in vivo sensor position. A telemetry unit 26 (FIG. 1) is coupled to the connector fitting 18 and functions to transmit glucose measurement signal information by means of radio telemetry. As viewed in FIG. 1, the telemetry unit 26 can transmit the glucose measurement information to the infusion pump 14 for closed loop operation thereof, or alternately to an externally located monitor 28. FIG. 1 illustrates the monitor 28 in the form of a wrist-worn device, although it will be understood that the monitor 28 may take other convenient forms. As is known in the art, the monitor 28 can be manipulated in response to information received and/or displayed thereby to control pump operation through the use of radio telemetry signals. In this regard, the monitor 28 may be programmed to automatically adjust pump operation according to glucose measurements, or to recommend a treatment program to allow patient verification and manual initiation, or to simply display the glucose readings and permit manual entry of reprogramming commands.

The glucose sensor 20 generally comprises, in one preferred form, an implantable enzyme electrode of the general type described in U.S. Pat. Nos. 4,650,547; 4,671,288; 4,781,798; 4,703,756; and 4,890,620 which are incorporated by reference herein. Such enzyme electrodes comprise an elongated sensor cable 30 (FIGS. 1 and 3) having a distal end defining a sensor tip for direct contact with patient fluid, such as blood. The sensor tip defines a conductivity sensor for measuring fluid conductivity changes in response to an enzymatic reaction typically involving the use of glucose oxidase to catalyze glucose in the presence of oxygen ($O_2$). Conductivity signals are transmitted through the cable via conductors 34 to a proximal end of the sensor cable.

Figure 3:
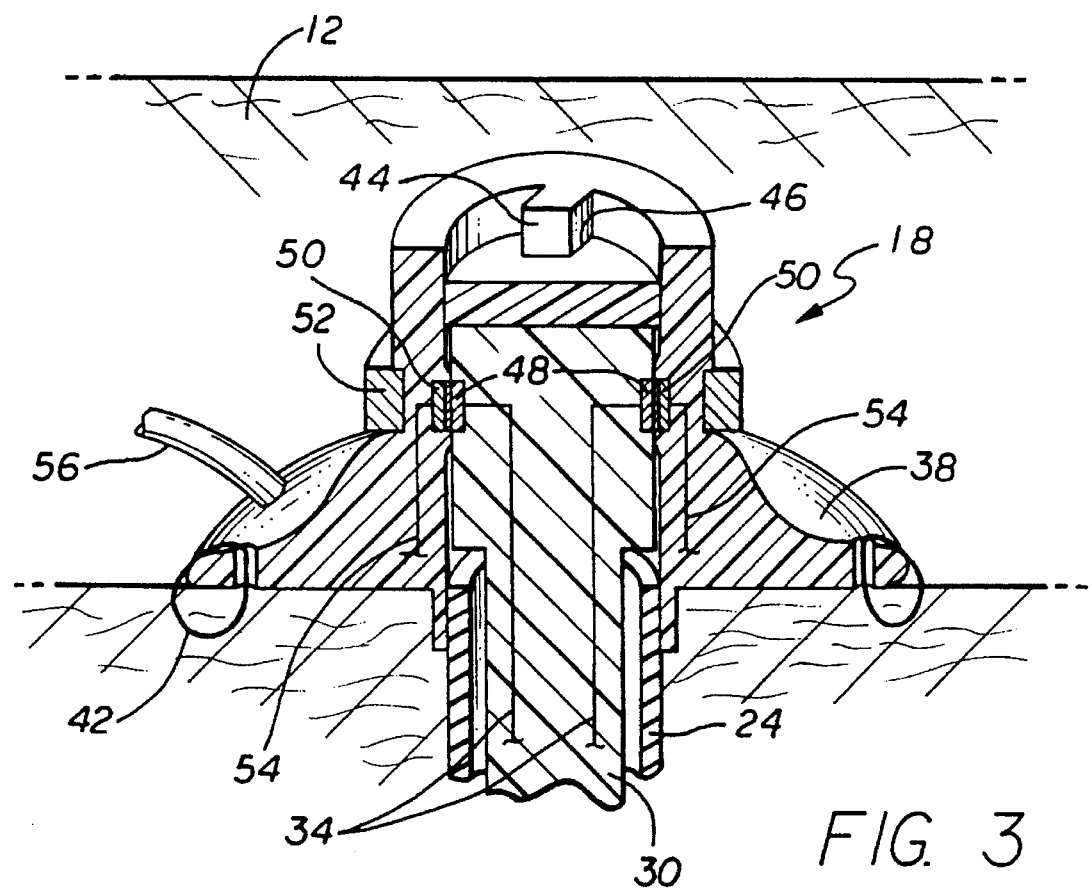
FIG. 3 is an enlarged fragmented sectional view similar to FIG. 2, and depicting a glucose sensor cable installed within the connector fitting.

As shown in FIGS. 2 and 3, the connector fitting 18 provides a convenient and relatively simple structure for anchoring the proximal end of the sensor cable 30 in electrical coupled relation with the telemetry unit 26. More particularly the illustrative connector fitting 18 is mounted at the proximal end of the catheter 24 and has a generally cylindrical shape defining a central bore 36 disposed in-line with the catheter. The sensor cable 30 may thus be introduced percutaneously for passage through the connector fitting 18 and catheter 24 to position the sensor tip 32 at the in vivo sensor site. In this position, the proximal end of the sensor cable 30 is seated and retained within the connector fitting (FIG. 3).

The connector fitting 18 includes a radially enlarged flange 38 having suture ports 40 formed therein to facilitate anchored connection of the fitting by sutures 42 or the like, to the subcutaneous muscle facia. An internal key 44 within the connector fitting 18 aligns with a mating key slot 46 in the sensor cable 30 to rotationally orient cable contacts 48 with mating contacts 50 within the connector fitting. An external lock ring 52 is conveniently provided for radially compressing the connector fitting 18 in the vicinity of the contacts 48 and 50 to ensure intimate electrical connection. The fitting contact 50 are connected in-turn via internal conductors 54 to an appropriate cable 56 leading to the telemetry unit 26. It will be understood, however, that alternative couplings may be provided for interconnecting the sensor with the connector fitting.

Figure 4:
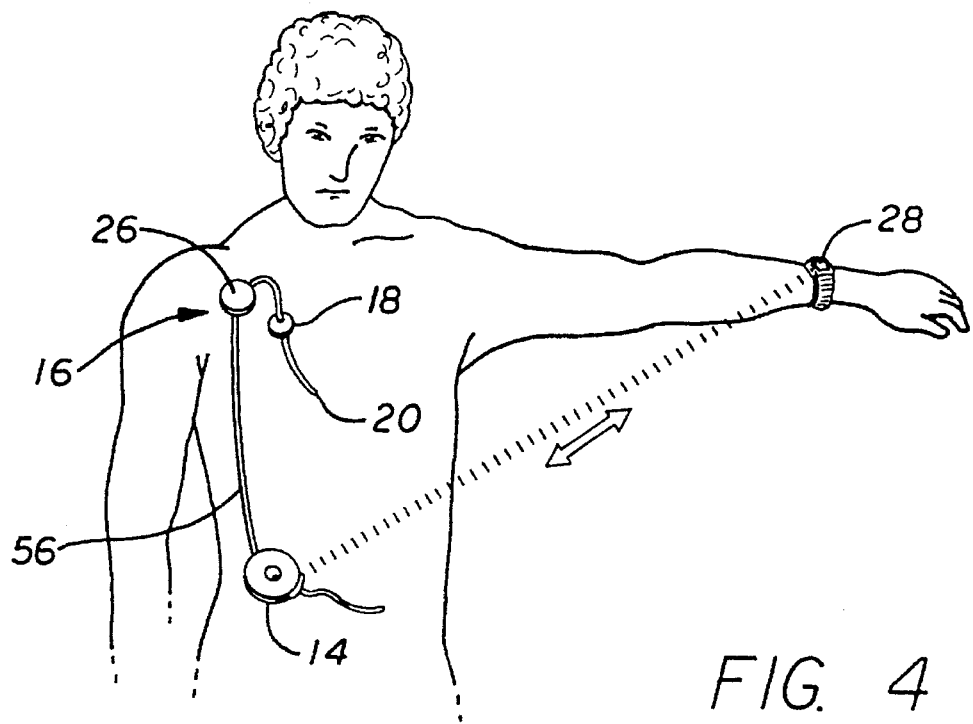
FIG. 4 is a schematic view similar to FIG. 1, but depicting an alternative preferred form of the invention.

FIG. 4 illustrates an alternative preferred form of the invention, wherein the cable 56 connected to the fitting 18 is connected directly to a control unit or circuit disposed internally within the implanted pump 14. With this system, radio telemetry transfer of glucose measurement information to the pump 14 is unnecessary. Instead, the information is transmitted directly through the use of the cable 56. Once again, the external monitor 28 may be used to read out or reprogram the pump 14 as previously described.

In either embodiment, the glucose sensor 20 can be accessed quickly and easily for periodic replacement. In this regard, the service life of the glucose sensor 20 is typically on the order of a few to several months, for a service period substantially less than the service life of an implanted pump 14. When sensor replacement is required, the sensor cable 30 is accessed through the skin of the patent for relatively easy sensor removal and insertion of a replacement sensor cable. Importantly, sensor removal and replacement is accomplished under the influence of a local anesthetic, and without requiring removal or replacement of any other system components.

A variety of further modifications and improvements to closed loop infusion pump system will be apparent to those persons skilled in the art. For example, it will be understood that the implanted sensor unit with removable sensor 20 can be used to provided glucose measurement information to an external monitor, and/or to an external pump. Moreover, the connector fitting may be provided as part of an integrated unit including the pump 14, whereby the sensor is disconnectable from the pump for removal and replacement, if desired. Accordingly, no limitations on the invention are intended by way of the foregoing description and accompanying drawings, except as set forth in the appended claims.

What is claimed is:

1. A system for delivering medication to a patient, comprising:

a sensor unit including implantable glucose sensor means for in vivo monitoring of a patient blood glucose parameter, an implantable connector fitting for supporting said sensor means within a patient to permit transcutaneous access to said sensor means for removal and replacement without removing said connector fitting from the patient, and control means coupled by said fitting to said sensor means for generating a signal representative of the monitored patient parameter; and pump means for administering medication stored therein to the patient, said pump means including means responsive to said signal to administer the medication in accordance with the monitored patient parameter;

said sensor unit further comprising a catheter having one end connected to said connector fitting and adapted to extend from said fitting generally to a selected in vivo sensing site within the patient, said sensor means comprising a sensor tip and cable means having a distal end thereof connected to said sensor tip and a proximal end for removable mounting within said connector fitting, said cable means extending from said fitting through said catheter.

2. The system of claim 1 wherein said control means is implantable.

3. The system of claim 1 wherein said pump means is implantable.

4. The system of claim 1 wherein said pump means and said control means are implantable.

5. The system of claim 1 wherein said signal comprises a radio telemetry signal.

6. The system of claim 1 further including means for securing said fitting at a selected subcutaneous position within the patient.

7. The system of claim 1 wherein said fitting has a generally cylindrical shape for receiving said proximal end of said cable means.

8. The system of claim 7 further including compression means for retaining said proximal end of said cable means within said fitting.

9. A system for delivering medication to a patient, comprising:

a sensor unit including implantable glucose sensor means for in vivo monitoring of a patient blood glucose parameter, an implantable connector fitting of generally cylindrical shape for supporting said sensor means within a patient to permit transcutaneous access to said sensor means for removal and replacement through said connector fitting without removing said connector fitting from the patient, and control means coupled by said fitting to said sensor means for generating a signal representative of the monitored patient parameter; and pump means for administering medication stored therein to the patient, said pump means including means responsive to said signal to administer the medication in accordance with the monitored patient parameter;

said sensor unit further comprising a catheter having one end connected to said connector fitting and adapted to extend from said fitting generally to a selected in vivo sensing site within the patient, said sensor means comprising a sensor tip and cable means having a distal end thereof connected to said sensor tip and a proximal end for removable mounting within said connector fitting, said cable means and said sensor tip having a size to fit through said connector fitting and said catheter.

\* \* \* \* \*